US010653551B2

(12) United States Patent
Apolinario et al.

(10) Patent No.: US 10,653,551 B2
(45) Date of Patent: May 19, 2020

(54) METHODS AND APPARATUSES FOR OSTOMY GAS MANAGEMENT

(71) Applicant: ENTRENOUS, LLC, San Francisco, CA (US)

(72) Inventors: Joan C. Apolinario, Evanston, IL (US); Rachel J. Blumberg, San Francisco, CA (US); Whitney R. Halgrimson, Chicago, IL (US)

(73) Assignee: ENTREMOUS, LLC, San Francisco, CA (US)

( * ) Notice: Subject to any disclaimer, the term of this patent is extended or adjusted under 35 U.S.C. 154(b) by 557 days.

(21) Appl. No.: 15/321,429

(22) PCT Filed: Jun. 23, 2015

(86) PCT No.: PCT/US2015/037078
§ 371 (c)(1),
(2) Date: Dec. 22, 2016

(87) PCT Pub. No.: WO2015/200255
PCT Pub. Date: Dec. 30, 2015

(65) Prior Publication Data
US 2017/0209294 A1 Jul. 27, 2017

Related U.S. Application Data

(60) Provisional application No. 62/016,069, filed on Jun. 23, 2014.

(51) Int. Cl.
*A61F 5/441* (2006.01)
*A61F 5/445* (2006.01)

(52) U.S. Cl.
CPC .............. *A61F 5/441* (2013.01); *A61F 5/445* (2013.01)

(58) Field of Classification Search
CPC ........ A61F 5/44–449; A61F 2005/4402–4495; A61F 5/441
See application file for complete search history.

(56) References Cited

U.S. PATENT DOCUMENTS

| 2,555,086 | A | * | 5/1951 | Edwin | ..................... | A61F 5/445 |
| | | | | | | 604/333 |
| 3,039,464 | A | * | 6/1962 | Galindo | ................... | A61F 5/448 |
| | | | | | | 604/344 |

(Continued)

FOREIGN PATENT DOCUMENTS

GB 2268882 A 1/1994

OTHER PUBLICATIONS

International Search Report and Written Opinion for Application No. PCT/US15/37078, dated Sep. 8, 2015.

*Primary Examiner* — Susan S Su
(74) *Attorney, Agent, or Firm* — Marshall, Gerstein & Borun LLP (57) ABSTRACT

A gas management system for use with an ostomy pouch includes an insert port defining an insert-receiving passage in communication with an inner chamber of an ostomy pouch and an exterior of the ostomy pouch. The insert port may be integrated into one or more walls of the ostomy pouch. An insert is selectively received in the insert-receiving passage of the insert port, the insert including at least one vent therein. An odor adsorbent element is disposed in the insert. The insert-receiving passage and the vent of the insert defining a pathway for gases passing from the inner chamber of the ostomy pouch and through the adsorbent material to pass out of the gas management apparatus. A guard may be supplied to carry a used insert upon removal from the insert port, as well as a replacement insert. The guard may have a wall to seal the used insert and the replacement insert. In certain embodiments, an applicator may be used to facilitate insertion of replacement inserts.

14 Claims, 9 Drawing Sheets

Cross-Sectional View

(56) References Cited

U.S. PATENT DOCUMENTS

| | | | | |
|---|---|---|---|---|
| 4,232,672 A | * | 11/1980 | Steer | A61F 5/441 604/333 |
| 4,328,828 A | * | 5/1982 | Cianci | A61F 5/441 137/549 |
| 4,411,659 A | * | 10/1983 | Jensen | A61F 5/441 604/332 |
| 4,451,258 A | * | 5/1984 | Jensen | A61F 5/441 55/385.4 |
| 4,516,974 A | * | 5/1985 | Davis | A61F 5/441 55/385.4 |
| 4,938,749 A | | 7/1990 | Jensen | |
| 4,986,824 A | | 1/1991 | Steer et al. | |
| 5,626,569 A | * | 5/1997 | Holtermann | A61F 5/441 251/262 |
| 5,658,267 A | | 8/1997 | Colacello et al. | |
| 5,690,621 A | * | 11/1997 | Canela | A61F 5/4407 604/333 |
| 5,733,271 A | * | 3/1998 | Bj.o slashed.rn | A61F 5/441 604/333 |
| 5,758,231 A | * | 5/1998 | Coffey | G03G 15/0898 399/106 |
| 5,840,073 A | * | 11/1998 | Olsen | A61F 5/441 604/333 |
| 6,165,159 A | * | 12/2000 | Blanton | A61F 5/441 604/333 |
| 6,241,712 B1 | | 6/2001 | Steer | |
| 6,659,988 B1 | * | 12/2003 | Steer | A61F 5/441 604/333 |
| 7,367,965 B2 | * | 5/2008 | Poulsen | A61F 5/441 604/322 |
| 10,004,629 B1 | * | 6/2018 | Carrero | A61F 5/442 |
| 2008/0275410 A1 | * | 11/2008 | Burt | A61F 5/4405 604/333 |
| 2010/0145291 A1 | * | 6/2010 | Kambara | A61F 5/441 604/333 |
| 2012/0277700 A1 | | 11/2012 | Amer, Jr. et al. | |
| 2013/0304008 A1 | | 11/2013 | Hanuka et al. | |
| 2013/0338615 A1 | * | 12/2013 | Zeller | A61F 5/4405 604/328 |
| 2015/0290024 A1 | * | 10/2015 | Nassopoulos | A61F 5/445 604/332 |
| 2015/0305916 A1 | * | 10/2015 | Hanuka | A61F 5/4401 604/333 |

* cited by examiner

Cross- Sectional View

Side view

PEN STORES CLEAN FILTERS

METHODS AND APPARATUSES FOR OSTOMY GAS MANAGEMENT

CROSS-REFERENCE TO RELATED APPLICATIONS

This application is a non-provisional that claims priority under 35 USC § 119(e) to U.S. provisional Application No. 62/016,069, filed Jun. 23, 2014. US provisional Application No. 62/016,069 is hereby incorporated by reference.

BACKGROUND

This patent is directed to methods and apparatuses for gas management, and in particular to methods and apparatuses for use with ostomy products for gas management.

During a patient's normal use of an ostomy pouch, significant volumes of gas can accumulate within the pouch. In turn, this can cause a ballooning effect of the pouch, which can cause ostomates distress for a number of reasons.

The ballooning effect causes a discretion issue, as it is difficult to conceal the pouch under clothing. This is concerning in social environments, where individuals may want to keep their ostomy private.

The expanded pouch is uncomfortable both during the day and at night. For example, at night, one may roll over onto the pouch, potentially causing the pouch to detach from the abdomen, causing fecal output to spill everywhere. If pressure is sufficiently high, stool can sometimes escape through pores of the filter as well.

The ballooning effect also reduces the usable wear period of an ostomy wafer and pouch, as the increased pressure causes the wafer to detach from the skin. A detached wafer requires the ostomate to exchange the full ostomy appliance (wafer and pouch), causing greater physical discomfort to the ostomate through skin irritation and increasing the cost of care through more frequent supply purchases.

The collected gas is also significantly odorous, and this leads to further restrictions and embarrassment for ostomates. For example, ostomates will avoid traveling to visit family or friends because they do not want to release the odorous gas in foreign bathrooms. Furthermore, a common method for addressing ballooning is to uncouple the pouch and vent the collected gas, but this must be done in absolute seclusion due to the embarrassing gas odor that is released.

In order to avoid accidents such as these, ostomates will often wake up in the middle of the night to relieve the pressure, which causes a disruption of normal sleep patterns. The normal daily routine also suffers numerous disruptions as the ostomate must frequently visit the restroom or find secluded environments to empty the gas from their pouch. Lastly, ostomates will significantly alter their diet in order to reduce their gas production on a daily basis.

There are no current solutions that prevent gas ballooning or address gas odor for the entire wear period of each pouch in a hygienic, affordable and easy-to-use way. The most prevalent current product is a charcoal filter that is integrated into the pouch. Integrated filters have a tendency to foul during the first day. Because of this fouling problem, the filter does not function for the full wear period of the pouch, which is often four to seven days. Valve solutions also exist, which must be installed by the user and require active manual intervention by the user in order to work. These valves effectively function as emergency release valves after ballooning has already occurred, and they do not address odor.

As set forth in more detail below, the present disclosure describes apparatuses and methods for gas management useful with ostomy products, but may be useful elsewhere, embodying advantageous alternatives to the existing methods.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF VARIOUS EMBODIMENTS

The embodiments of the gas management apparatuses and methods described herein use material to absorb odorous gases, while optionally allowing the passage of other gases through. The odorous gases may include those produced by the intestine, such as hydrogen sulfide ($H_2S$) and methyl mercaptan (MeSH). As a consequence, the gas management apparatus may prevent ballooning from occurring while minimizing user exposure to unpleasant odorous gases.

The embodiments of gas management apparatus include an insert (or unit, or filter (depending on the use of the insert)) and an insert port (or port). The insert port is attached (e.g., joined by adhesive or heat-seal or weld) to an ostomy product, such as an ostomy pouch. The insert port has a passage in which the insert is disposed. The passage is in communication with an inner chamber of the ostomy product, such that gases (and potentially other materials) contained in the ostomy product may pass from the inner chamber and into the insert port passage. The insert is disposed within the passage in such a way that most (e.g., at least 50%) if not all of the gases that pass into the passage also come in contact with the insert, and in particular with a portion of the insert formed of an odor adsorbent. The insert port may include a latch that attaches or secures the insert in place in the passage.

It should be recognized that while in many of the embodiments of the gas management apparatus described below the insert port is open, such that gases flow into and through the passage and out of the ostomy product via the insert port, this may not be the case according to all embodiments of the present disclosure. For example, the insert port may be closed or capped, such that gases may enter the port, but are unable to exit the ostomy product. In such a circumstance, the odorous gases may still be exposed to the odor adsorbent, thereby removing at least a portion of the odorous gases from the inner chamber of the ostomy product.

The insert is intended to be disposable, when the insert becomes fouled, such as when the individual using the ostomy product lies down, for example. In addition, more than one insert may be used with a single ostomy product over the life of the ostomy product. To this end, the insert may be used in conjunction or combined with an applicator that facilitates the removal and/or disposal of the existing insert and the placement of a new insert in the insert port. The applicator would enable these actions to be performed in a hygienic manner. For example, the applicator may cause the existing insert to be pushed through the passage in the insert port and into the inner chamber of the ostomy product (so that the insert may be disposed of with the intestinal wastes collected in the ostomy product), while a new insert is moved into place in the passage of the insert port. According to other embodiments, the insert may be detached from the port and disposed of in a refuse container.

Figures 1, 2:
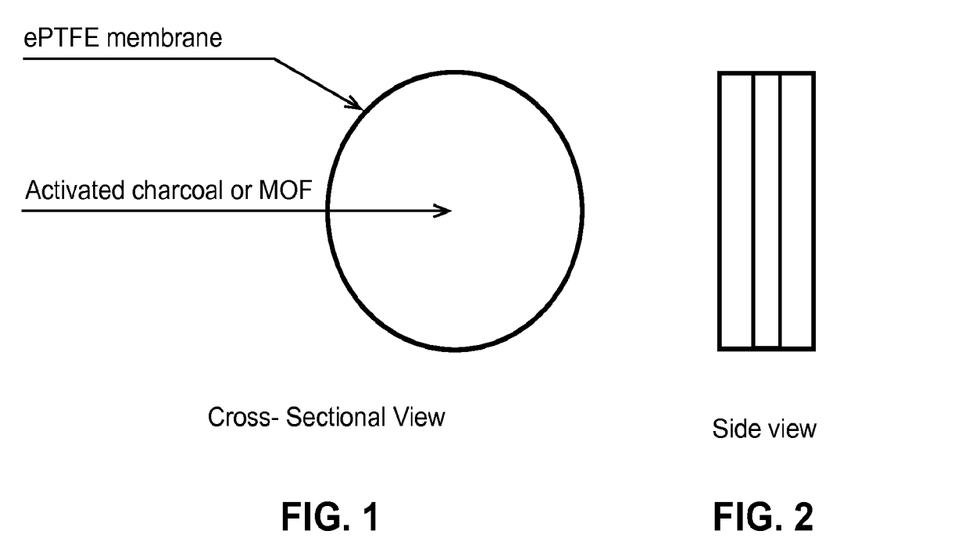
FIG. 1 is a frontal view of an embodiment of an insert for use with a gas management apparatus.
FIG. 2 is a cross-sectional view of the insert of FIG. 1.

The insert may include a liquid-impermeable, gas-permeable layer or membrane that encapsulates the odor adsorbent. For example, as illustrated in FIGS. 1 and 2, the odor absorber is entirely encapsulated or covered with the liquid-impermeable, gas-permeable material. According to other embodiments, the odor adsorbent may only partially encapsulate or cover the odor adsorbent.

The odor adsorbent used in the inserts describe herein may include, by way of explanation and not by way of limitation, activated charcoal, zeolites and metal-organic frameworks (MOFs).

Activated charcoal, zeolites and MOFs can be used to selectively sequester and store gas particles. Human gas is mainly comprised of nitrogen, carbon dioxide, methane, and hydrogen. The odorous portion of the gas is mainly comprised of hydrogen sulfide, methanthiol, and skatole, though they represent <5% of the output. It has been shown in the literature that these gases can be sequestered using activated charcoal, zeolites or MOFs.

Zeolites and MOFs have gas storage capacities that may be particularly favorable. It is documented that the storage capacities of up to 4 mmol/kg (mmol gas per kg of media) can be achieved with zeolites and/or MOFs.

While zeolites and MOFs have a well-documented ability to adsorb gases, their overall shape, weight, and potential for hydrophobicity permits their advantageous use in, for example, ostomy products as described herein. Hydrophobicity may be particular important as commercially-available gas management technology for ostomy pouches are believed to cease function post-contact with liquid.

The embodiments described herein may use a particular type of activated charcoal, zeolite or MOF, or may use a combination of activated charcoal, zeolites and/or MOFs together to capture the heterogeneous gas mixture that frequently comprises ostomy output.

The membrane that surrounds the gas adsorbent is microporous membrane (such as ePTFE Gore-Tex) that may be hydrophobic and oleophobic, but is gas permeable. This membrane serves to protect the gas adsorbent from intestinal output on the interior of the pouch. This membrane also serves to protect the gas adsorbent on the exterior portion of the pouch from things such as water or sweat from daily activities. Due to the porous nature of the material, passage of gases through the filter can still occur. The filter can be comprised of membrane/adsorbent/membrane as shown in FIGS. 1 and 2, or can continue to alternate in many layers to ensure prevention of leakage (not shown). The layers of membrane and adsorbent can be unified by adhesive, heat sealing, or pressure from an additional casing unit. The shape of the filter is shown as a disk. Generally, sealing is more easily achieved with mating of parts of cylindrical nature. However, it is possible for sealing to occur with different geometry, so potential embodiments are not limited to disks.

As mentioned above, the gas management apparatus may also be capped. According to such an embodiment, a MOF that specifically adsorbs both odorous and volumous gases produced by the intestine (primarily hydrogen ($H_2$), nitrogen ($N_2$), methane ($CH_4$) and carbon dioxide ($CO_2$)) may be used because there will be minimal or no outflow of any gases. An embodiment of an insert for such a capped apparatus may follow similar geometry as above with a protecting microporous membrane over the internal aspect of the unit, protecting the MOF from intestinal output. The external aspect of the unit would be solid material (i.e. plastic) that does not permit the passage of gases or liquids (e.g. acts as a "cap"). The cap would protect the contained MOF from external elements, and it would also protect the user and environment from possible exposure to pouch contents by preventing leakage of intestinal output and odor.

In fact, the port may be capped using an insert that does not permit through-passage of gas during those times when ostomates may wish to not vent, for example, when they are sleeping or showering.

Figure 3:
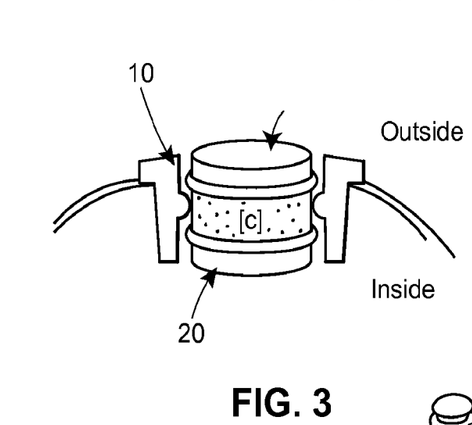
FIG. 3 is a partial cross-sectional view of an embodiment of a gas management apparatus including a disposable insert disposed in an insert port, the port attached to an ostomy product, such as an ostomy pouch.
Figure 4:
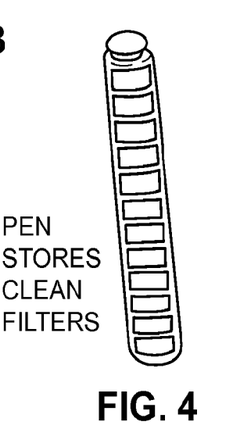
FIG. 4 is an applicator for use with the insert of FIG. 3.
Figure 5:
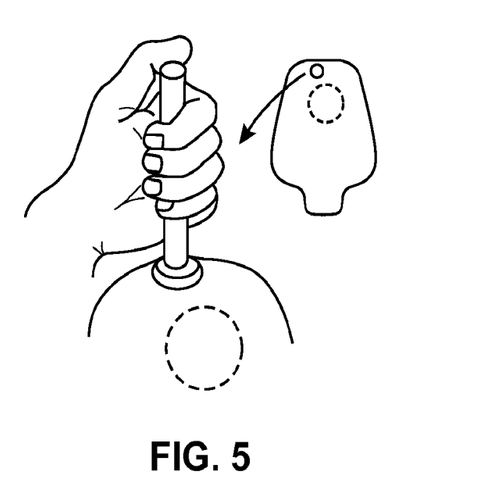
FIG. 5 is a perspective view of the applicator of FIG. 4 in use with an ostomy product, such as an ostomy pouch, including a gas management apparatus as illustrated in FIG. 3.

FIGS. 3-5 illustrate a first embodiment of a gas management apparatus including an insert port 10 and an insert 20. FIG. 3 illustrates an insert port according to this embodiment attached to a wall of an ostomy product, such as an ostomy pouch, with an insert disposed within the passage. O-rings may be incorporated into the insert to seal against an inner surface of the insert port to limit leakage. FIG. 4 illustrates an applicator that may be used with the insert of FIG. 3, which applicator may also be used as a storage device. FIG. 5 illustrates the introduction of a new insert to the insert port in the pouch, which is done by pushing while the pouch is on the ostomate. Pushing a new insert into the port causes the old insert to fall into the pouch. The old insert is then disposed of, for example in the toilet, at the individual's convenience.

FIGS. 6-9 illustrate a second embodiment of a gas management apparatus including an insert port 30 and an insert 40.

Figure 6:
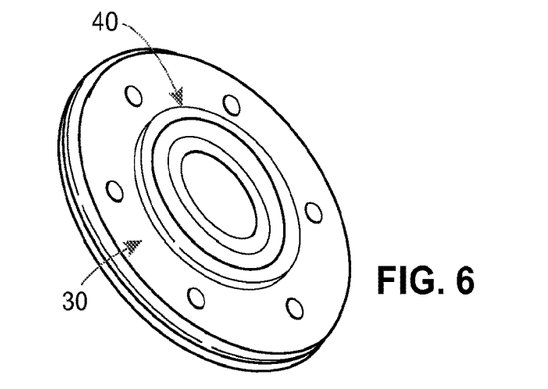
FIG. 6 is a perspective view of another embodiment of a gas management apparatus including a disposeable insert disposed in an insert port, the port being attachable or attached to an ostomy product, such as an ostomy pouch.
Figure 7:
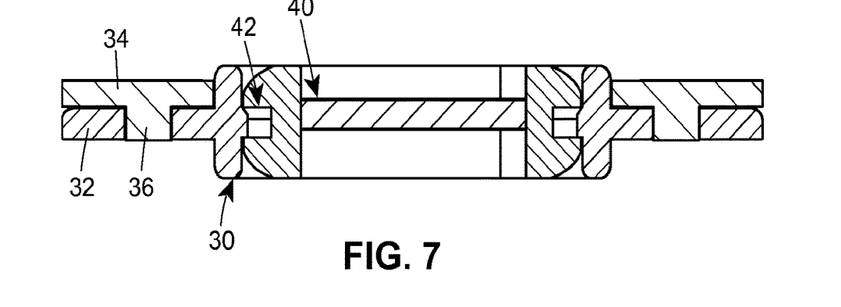
FIG. 7 is a cross-sectional view of the gas management apparatus according to FIG. 6.

FIGS. 6 and 7 illustrate the port 30, which may include two annular or ring-like parts 32 and 34. Sealing is achieved via snap fit of the first and second pieces 32, 34, sandwiching the ostomy pouch wall therebetween. The sealing may be further secured through the use of an adhesive at each post 36. Alternatively, the port can be adhered or heat-sealed to the pouch wall, using only the part 32. The port can be comprised of materials such as nylon, which are durable, light-weight, and rigid, to ensure that no leaks occur. Alternatively, the port can be comprised of a more flexible but durable material such as silicone, to increase comfort to the user.

As also best seen in FIG. 7, the portion of the insert that comes in contact with the port (also referred to as the housing) is comprised of rubber or flexible polymer, to create a seal within the port. The geometry of the insert housing against the port inner surface at 42 allows the user to snap the insert into place, creating a seal. There are multiple possible embodiments of a mechanism to provide the user with feedback that the insert is correctly and securely in place. An audible "snap", a "snap-in" sensation, or a threaded screw-in mechanism are examples of such possible embodiments. A curve along the entrance of the port helps to guide the insert into place. The platform face on the other end of the port prevents the insert from falling out of the port after it has been installed, and achieves a seal.

Figures 8, 9:
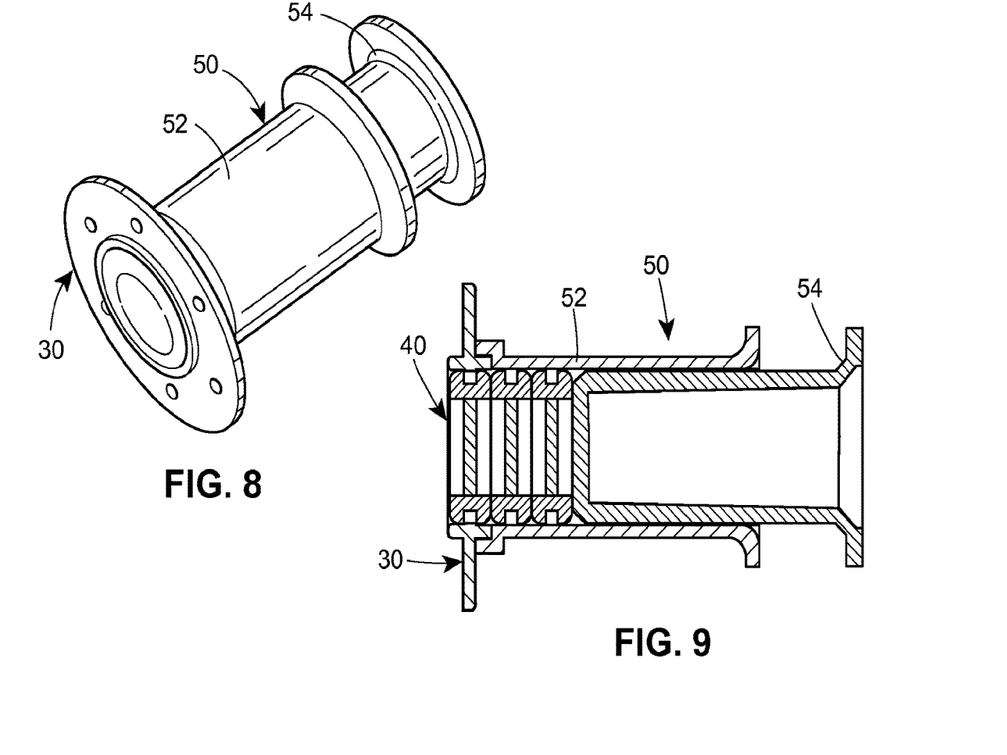
FIG. 8 is a perspective of the gas apparatus according to FIG. 6 in combination with an applicator for use with the disposable inserts illustrated in FIG. 6.
FIG. 9 is a cross-sectional view of the gas management apparatus and applicator as illustrated in FIG. 8.

As seen in FIGS. 8 and 9, the applicator 50 allows for storage of new filter or capped units and aids with alignment. The storage portion 52 of the applicator contains the inserts and latches onto the outer side of the port (see FIG. 9). Alternatively, the storage device can be screwed on to the port to ensure attachment. Attachment of the storage also serves to ensure secure and correct insertion of a new filter. A ridge at the bottom of the pouch ensures that inserts will not fall out of the storage portion 52 prior to application. The pusher 54 allows the user to push a new insert 40 into place. This can be done by simply pushing the pusher 54 in the direction of insertion. However, it is also possible to thread the storage portion 52 and the pusher 54 together such that turning the pusher 54 relative to the storage portion 52 will cause the insert to be put into place. The pusher 54 is hollow to allow the applicator 50 to be light-weight and use of less material. The port geometry is dimensioned such that insertion of a new insert causes the old insert to fall into the pouch. The applicator can be made of any rigid, durable, light-weight plastic, such as nylon.

Figure 10:
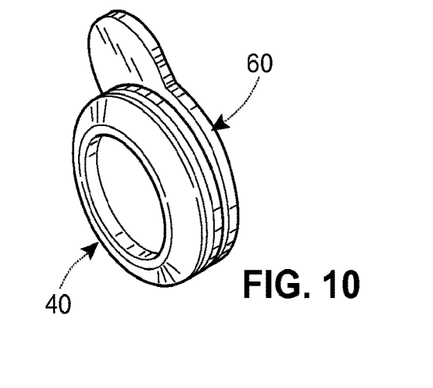
FIG. 10 is a perspective view of a disposable insert, similar to that illustrated in FIG. 6, in combination with an single-unit applicator.
Figure 11:
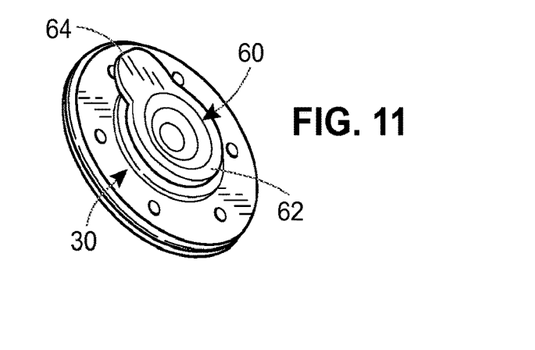
FIG. 11 is a perspective view of the insert and single-unit applicator of FIG. 10 in combination with an insert port similar to that illustrated in FIG. 6.
Figure 12:
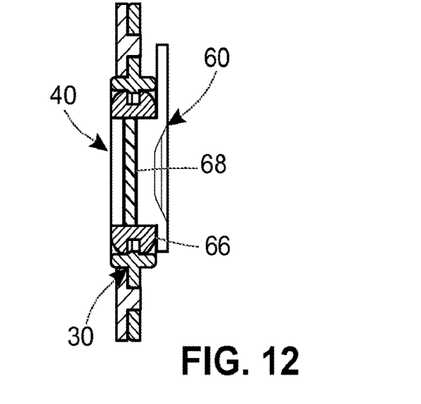
FIG. 12 is a cross-sectional view of the insert, insert port and single-unit applicator of FIG. 11.
Figure 13:
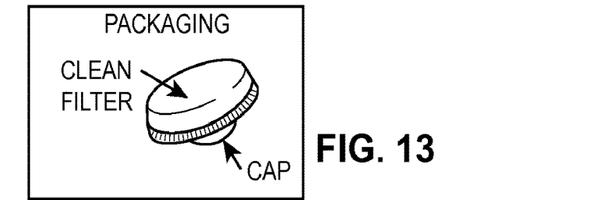
FIG. 13 is a perspective view of a disposeable insert according to another embodiment of a gas management apparatus.
Figure 14:
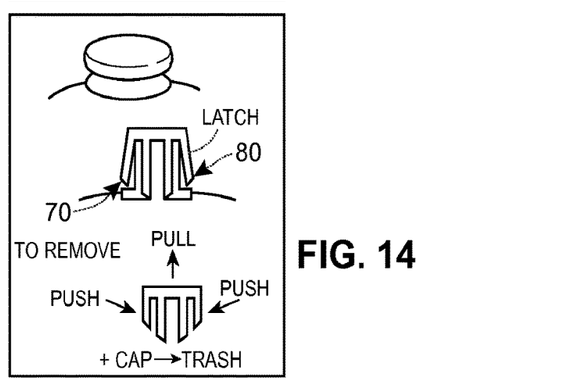
FIG. 14 is a cross-sectional view of the insert according to FIG. 13 in combination with an insert port.
Figure 15:
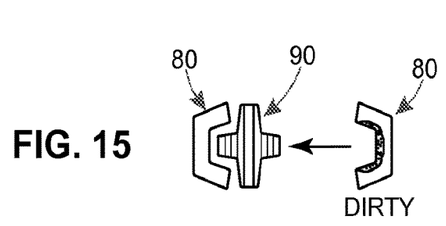
FIGS. 15-17 are partial cross-sectional views illustrating the use of a guard with an insert as illustrated in FIGS. 13 and 14.

Alternatively, the inserts 40 can be applied to the port 30 using an applicator 60 such as what is shown in FIGS. 10-12. As seen in FIG. 11, the user stabilizes the applicator 60 by pressing in the groove 62 with their middle finger while grasping the tab 64 with their index finger and thumb. Once aligned with the port, the user then pushes the insert into place. The user then pulls the tab back to the right (as illustrated in FIG. 12) to remove the applicator, which can then be disposed of. This applicator can be made of any light-weight plastic or rubber. The applicator rim 66 (see FIG. 12) is dimensioned to ensure the user does not push too far through, such that a new insert is not wasted, and the user is protected from coming in contact with intestinal output.

The applicator 60 could also be composed of dissolvable or rapidly-degrading material, such that it is safe to flush into the septic system, to improve user discretion in public settings.

In the diagram, the applicator 60 is held in place via the hub 68 (see FIG. 12) extending into the unit housing, relying on part fit. Alternatively, the applicator could be simply a sheet of a material such as a plastic in a similar shape, which is adhered or heat-sealed onto the outer rim of the insert housing (similar to what exists on pudding cup packaging). By keeping the sheet taut, the sheet becomes the support for application that the user needs to push the insert into place.

In this embodiment, old inserts (and their housing) are thrown away after replacement.

FIGS. 13-18 illustrate a further embodiment of a gas management apparatus including an insert port 70 and an insert 80. As see in FIGS. 13 and 14, this embodiment includes an insert that attaches to a latch on an outer surface of the insert port while also extending into the passage of the insert port. In particular, an elongated hub extends into the passage of the insert port, which hub may be hollow and may have an odor adsorbent material disposed therein according to certain embodiments. The insert also includes a skirt disposed about the hub, which skirt cooperates with the outer surface of the insert port to secure the insert into place. A variety of latching mechanisms may be used.

Figure 16:
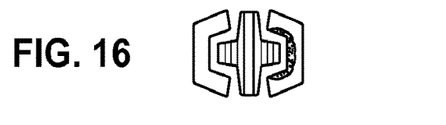
Figure 17:
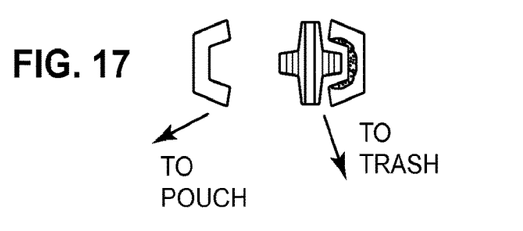
Figure 18:
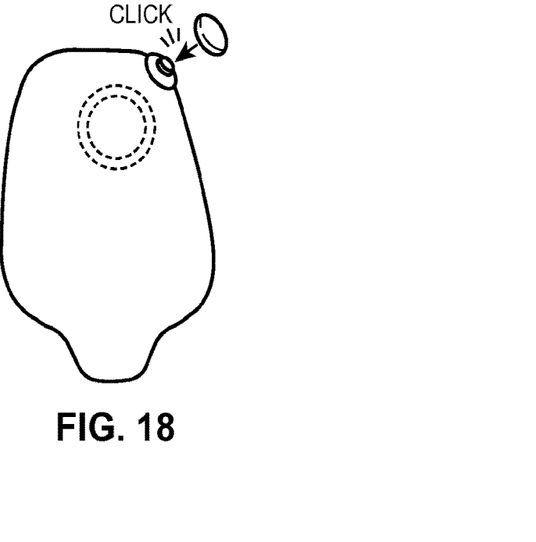
FIG. 18 is a perspective view of an ostomy product, such as an ostomy pouch, including the insert port and insert illustrated in FIGS. 13 and 14.

The insert 80 may be used with a guard (or carrier) 90 to facilitate disposal of the user insert while providing a new replacement. As seen in FIG. 16, the ostomate puts the used insert on the right end of the guard. Fecal output on the used insert is preferably completely encapsulated thereby, so the user does not touch the fecal output or smell it. Such a guard would also serve to prevent odor escape from the used filter before the trash receptacle is emptied, thus maintaining a more odor-free environment. As seen in FIG. 17, the user separates new insert on the left from guard, and the user puts new unit on pouch as in FIG. 18.

Figure 19:
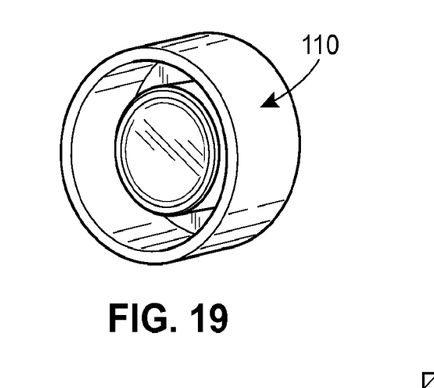
FIG. 19 is a perspective view of a disposeable insert according to a further embodiment of a gas management apparatus.
Figure 20:
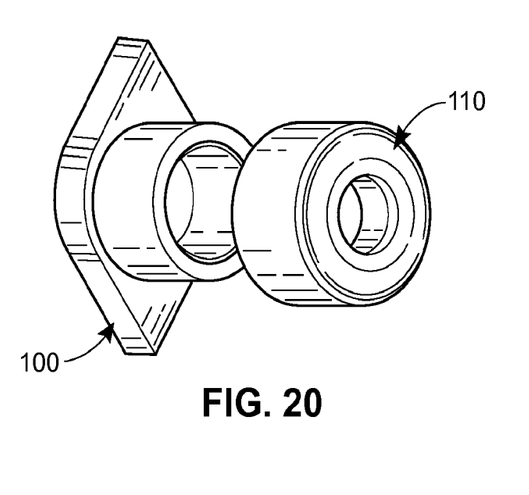
FIG. 20 is a perspective view of the insert of FIG. 19 and an insert port according to the further embodiment of a gas management apparatus.
Figure 21:
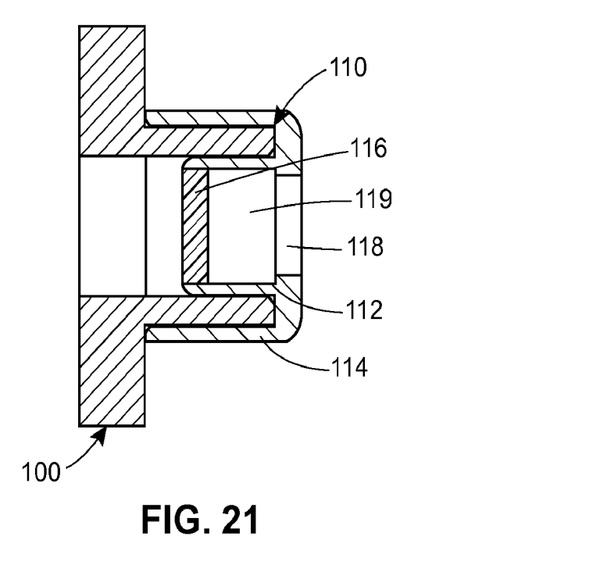
FIG. 21 is a cross-sectional view of the insert and insert port according to FIG. 20 with the insert assembled with the insert port.
Figure 22:
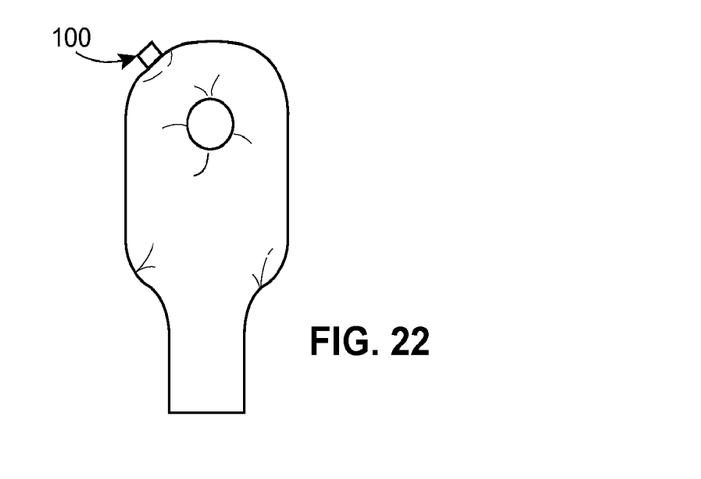
FIG. 22 is a perspective view of the insert according to FIG. 19 in combination with an ostomy product, such as an ostomy pouch.

FIGS. 19-25 illustrate a further embodiment of a gas management system including an insert port 100 and an insert 110. As seen in FIGS. 19-21, the insert 110 is similar to that of FIGS. 13 and 14, in that the insert 110 has an inner hollow hub 112 that is received within the passage 102 in the insert port 100, and an outer skirt 114 that fits about the outer surface of the insert port, the port thus being disposed between the hub and the skirt. An odor adsorbent 116 is received within the hub and the hub is open to allow gases to pass through the hub, the odor adsorbent and out of the insert. FIG. 22 illustrates the insert port attached to an ostomy product, such as an ostomy pouch.

According to this embodiment, the insert housing also snaps onto the port integrated to the pouch. The insert housing geometry keeps fecal matter stuck on used units far from the hands of the user, as the innermost edge of the hub 112 (where feces would collect) is shorter in length that the outwardmost edge of the skirt 114 that is handled by the user's fingers. An optional additional barrier for unit protection may be disposed at 118. The optional barrier may be a gas-permeable, liquid-permeable membrane such as the membrane used to encapsulate the odor adsorbent, to prevent water collection in the cavity 119 that could occlude airflow. Alternatively, the insert can fill the entire space of the cavity, allowing for multiple layers that can aid in leak prevention.

The "eye-shaped" geometry of the port allows for easy sealing of the port between the two pouch walls at the top portion of the pouch (see FIG. 22). This seal can be achieved through adhesive or heat-sealing. The portion of the port also serves as a base that the user can hold onto when removing or a new insert.

This port is placed at the top portion of ostomy pouch, between the two layers of plastic that comprise the pouch walls, as gas rises to the top of the pouch when a person is upright during the day. This position is also easiest for ostomates to see while the pouch is on their body, in order to handle the product during filter replacement.

Figure 23:
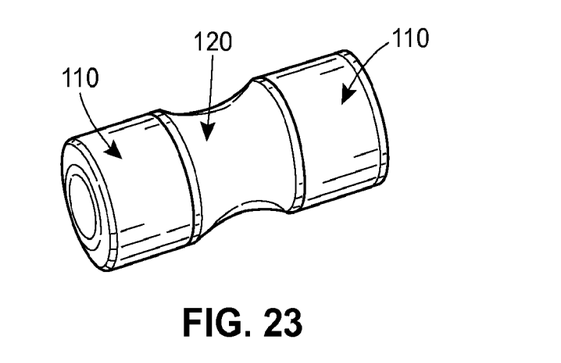
FIG. 23 is a guard for use with inserts such as illustrated in FIG. 19, with an insert attached to either end of the guard.
Figure 24:
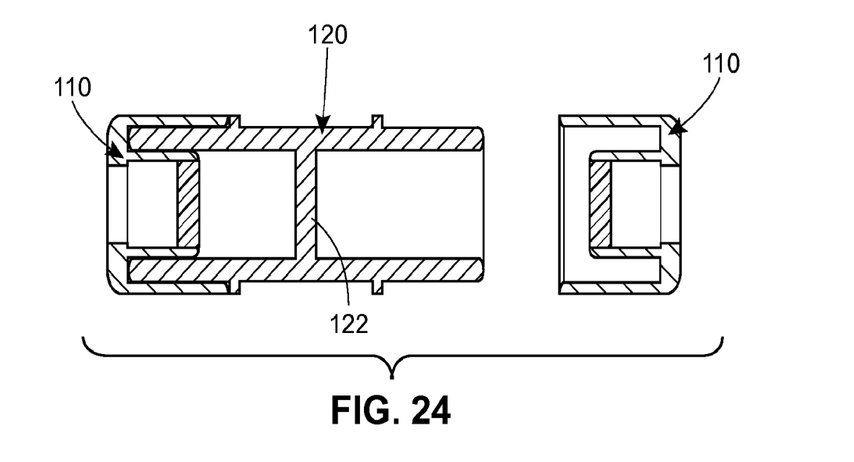
FIG. 24 is a cross-sectional view of the guard and inserts of FIG. 23 with one of the inserts separated from the guard.
Figure 25:
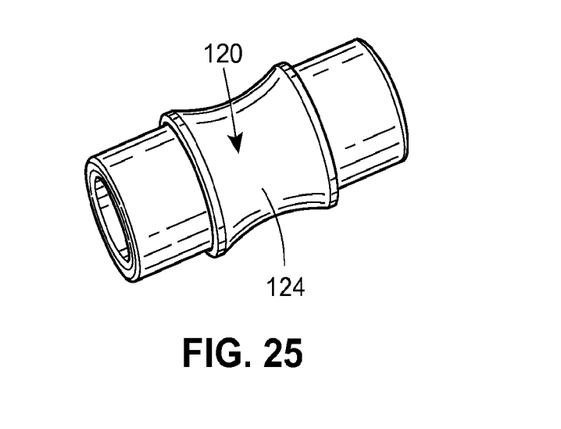
FIG. 25 is a perspective view of the guard illustrated in FIG. 23 without any inserts attached.

As shown in FIGS. 23-25, a guard 120 may be provided that allows for protection of a replacement insert 110, as well as storage of a fouled insert 110 until such time as the insert 110 may be disposed of. The insert housing may snap onto this guard 120 using a press-fit mechanism. Alternatively, a seal can be achieved using a screw-on mechanism. Both mechanisms may ensure tightness and correctness of fit through feedback mechanisms, such as auditory or physical sensations.

A middle wall 122 (see FIG. 24) creates a seal for the fouled unit, such that when the fouled unit is disposed with the guard, no odors escape. It also protects the new unit from any particulate matter prior to use. Additionally, the indentation, recess or saddle 124 disposed about part of or the entire circumference of the middle of the guard (best seen in FIGS. 23 (partial) and 25 (entire)) allows for easier handling when pulling off or pushing on the snap filter housing.

Figure 26:
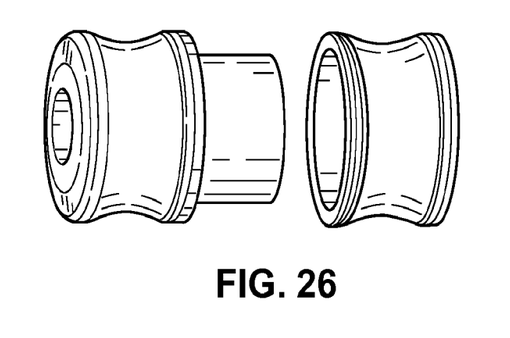
FIG. 26 is an alternative embodiment of a guard for use with inserts as illustrated in FIG. 19, with one of the inserts separated from the guard.
Figure 27:
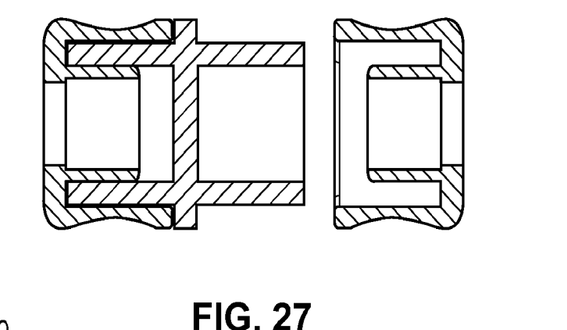
FIG. 27 is a cross-sectional view of the guard and inserts illustrated in FIG. 26.
Figure 28:
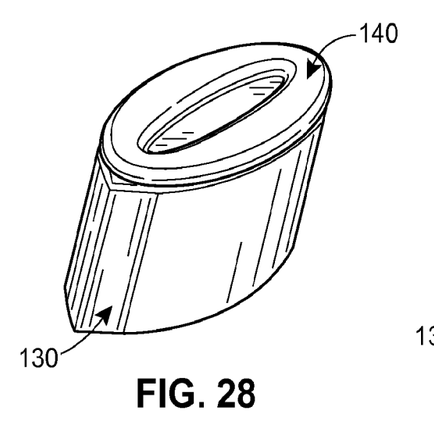
FIG. 28 is a perspective view of yet another embodiment of a gas management apparatus including an insert port and disposable insert.
Figure 29:
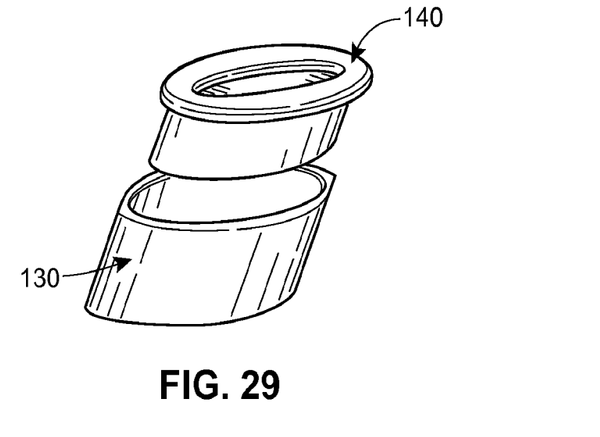
FIG. 29 is a perspective view of the apparatus of FIG. 28 with the insert separated from the insert port.

Alternatively, the new guard itself can serve as that means for handling, as shown in FIGS. 26 and 27. This eliminates the need for the indentation or saddle 124 on the guard 120, saving space, making a more discreet option that is easier to store, such as in a pocket.

The components for the embodiment of FIGS. 19-27 (port, guard, and insert housing) can be constructed using any durable, heat-sealable, light-weight plastic, such as nylon.

Figure 33:
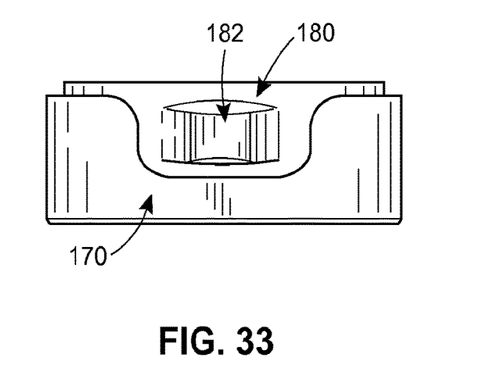
FIG. 33 is a still further embodiment of a gas management apparatus including an insert port and disposeable insert.

FIGS. 28-31 illustrate an embodiment of a gas management apparatus similar to that of FIGS. 19-22, with an associated guard illustrated in FIG. 33 that is similar to the guards illustrated in FIGS. 23-27. The apparatus includes a port 130 and an insert 140, which insert 140 may also be combined with the guard 150.

Using an oblong shape for the port 130 may permit for a more slim profile while maintaining enough surface area to allow for significant gas flow. In this embodiment, the outer walls of the port 130 are adhered or heat sealed to the pouch walls, such that the only portion that sticks out of the pouch is the rim on the unit housing. In order to facilitate handling of the unit housing, ridges that create texture or a tacky coating (such as silicone) on the outer rim (not shown) can be added.

Unlike, the port 100 and insert 110, the wall of the port 130 is not received between a hub and a skirt of the insert 110. Instead, the wall of the hub 142 of the insert 140 is received between inner and outer walls 132, 134 of the port 130, with a latch 136 (which may be in the form of a pair of facing ridges formed on facing surfaces of the inner and outer port walls 132, 134) provided to capture a ridge 144 formed at the innermost edge of the hub 142 to limit the ability of the insert 140 from being removed from the port 130. The cooperation between the latch 136 and the ridge 144 aids the user when installing/removing by creating a gradual sliding mechanism that ultimately pops into or out of place. One or more additional ridges 138 may be provided on the inner and/or outer walls 132, 134 below (i.e., further inwardly of) the first set of ridges that defines the latch 136, the ridges 138 assisting in maintaining a seal and from the user attempting to push too far. This configuration creates a tangible sensation and/or an auditory sensation (e.g. a "click") to assure the user that the unit has been properly installed. Ridges on the port 130 and the insert 140 may be created using the same material as the port 130 and the insert 140, or using o-rings.

Figure 30:
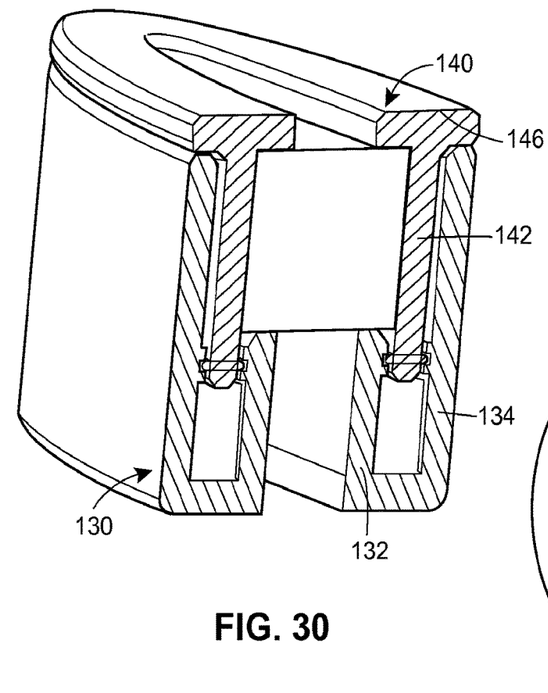
FIG. 30 is a cross-sectional view of the apparatus of FIG. 28.
Figure 31:
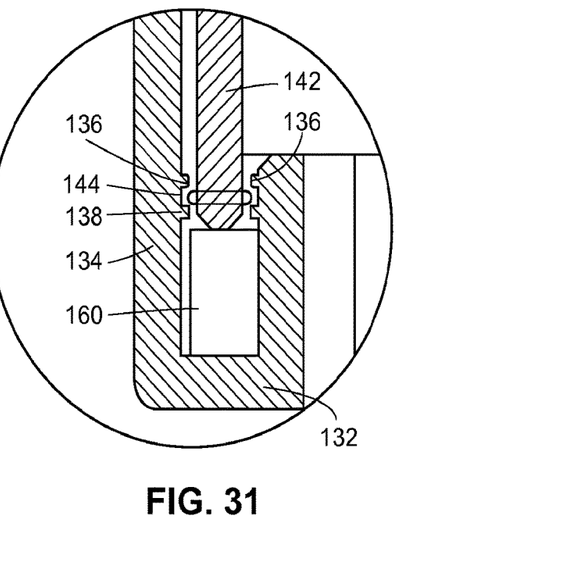
FIG. 31 is an enlarged, cross-sectional view of the apparatus of FIG. 28.

An o-ring 160 below the ridges 138 between the walls 132, 134 also aids in sealing the insert 140 to the port 130. The o-ring 160 is dimensioned such that it is flush against the insert housing and port. Pressure from the insert causes expansion of the o-ring radially, creating a seal. Of course, other or additional mechanisms for sealing may be provided to make to ensure that fecal matter does not leak (a concern for ostomates). For example, an outer edge 146 of the insert 140 may be flush against an outermost edge of the port to create a seal.

The insert outer edge 146 of the insert 140 may be in the form of an outwardly-directed lip region. The insert 140 may further be defined by an inwardly-directed lip region. At least a portion of the outer wall 134 is taller than the inner wall 132. The outwardly-directed lip region engages a top of the outer wall 134 and an odor adsorbent element 116 is secured intermediate the inner wall 132 of the insert port 130 and the inwardly-directed lip region of the insert 140.

Figure 32:
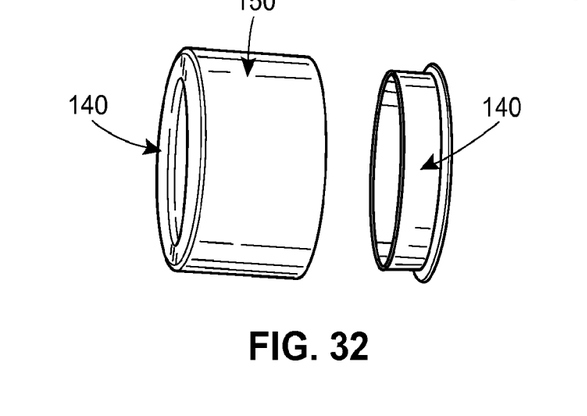
FIG. 32 is a guard for use with inserts as illustrated in FIG. 28.

FIG. 32 is a partially-exploded view of a removed insert 140, a guard 150, and a replacement insert 140.

Figure 34:
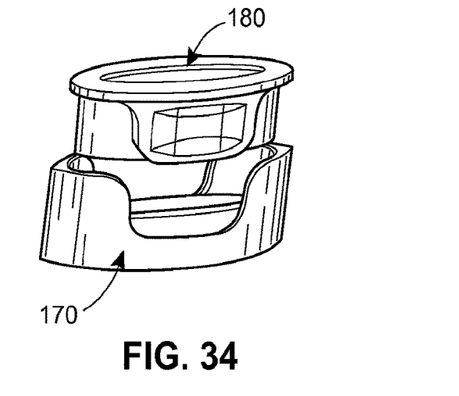
FIG. 34 is the gas management apparatus according to FIG. 33 with the insert separated from the insert port.
Figure 35:
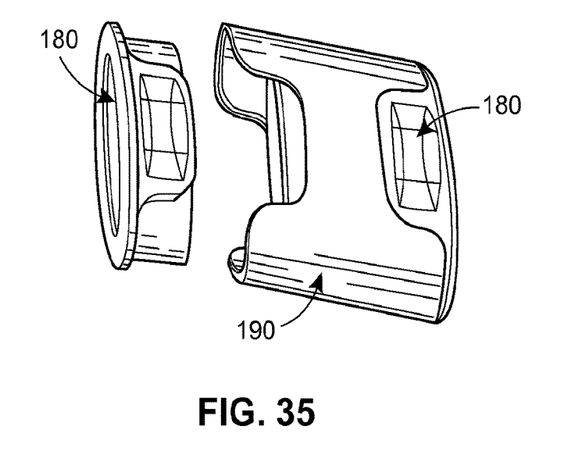
FIG. 35 is a guard for use with the inserts as illustrated in FIG. 33.

FIGS. 33-35 illustrate an embodiment of a gas management apparatus (port 170, insert 180) and guard 190 similar to that described in regard to FIGS. 28-32, but with an alternative geometry. In particular, grips 182 are provided to facilitate handling of the insert 180. In order to facilitate handling of the insert housing, ridges or a tacky coating (such as silicone) can also be added to the outer portion of the housing. A smooth indentation on the grips aid the user in the alignment of their fingers for installation/removal. The grips 182 are received in complementary grip-receiving channels in the outer wall 134 of the insert port 130.

Figure 36:
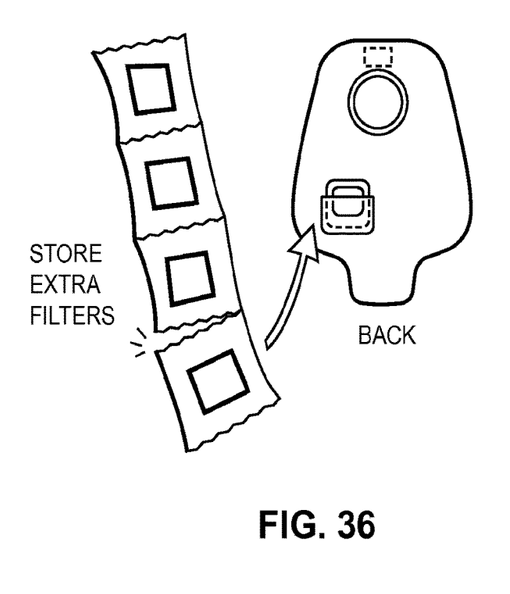
FIG. 36 is an embodiment of a gas management apparatus attached to an ostomy product, such as an ostomy pouch, with set of disposable inserts.
Figure 37:
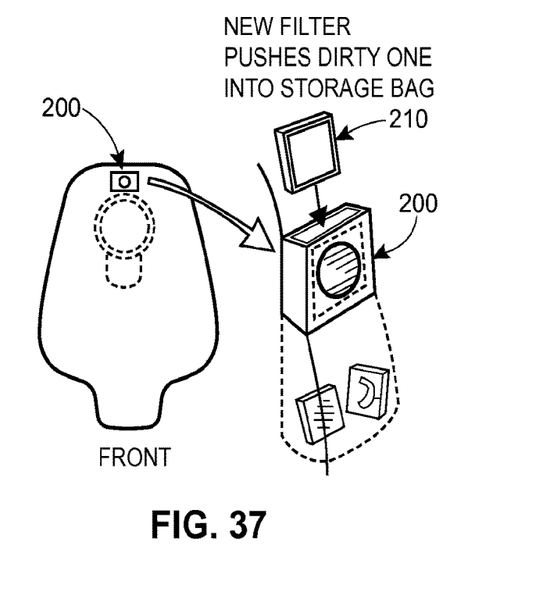
FIG. 37 is partial view of the gas management apparatus of FIG. 36, illustrating the operation of the insert port and insert.

FIGS. 36-40 illustrate a further embodiment of a gas management apparatus including an insert port 200 and an insert 210. As illustrated in FIG. 36, each insert may be stored individually in perforated plastic packaging, and may even be stored in a pocket on the wall of an ostomy product (e.g., pouch). As illustrated in FIG. 37, the user inserts a new insert into the top of the port, displacing the used insert. The used insert may fall into a pouch provided either on the inside or outside of the ostomy pouch, containing odors. Alternatively, the used insert may fall directly into the ostomy pouch, for disposal when the contents of the ostomy pouch are disposed of.

Figure 38:
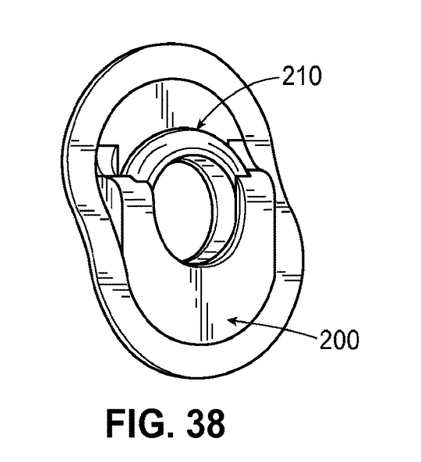
FIG. 38 is an insert port for use in an embodiment similar to that illustrated in FIG. 36 with an insert disposed therein.
Figure 39:
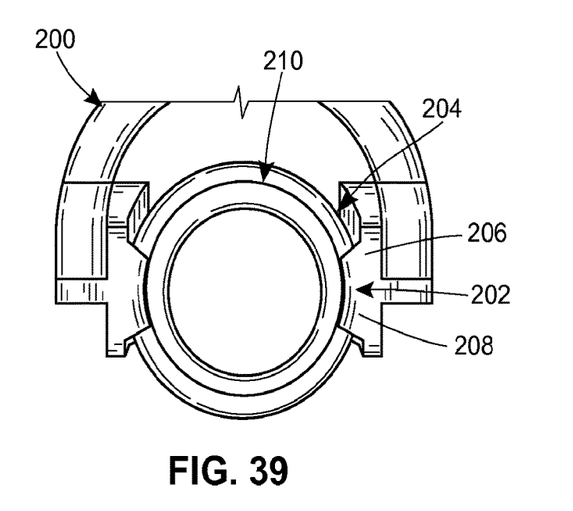
FIG. 39 is a cross-sectional view of the insert port and insert of FIG. 38 illustrating the cooperation of the insert with the insert port.
Figure 40:
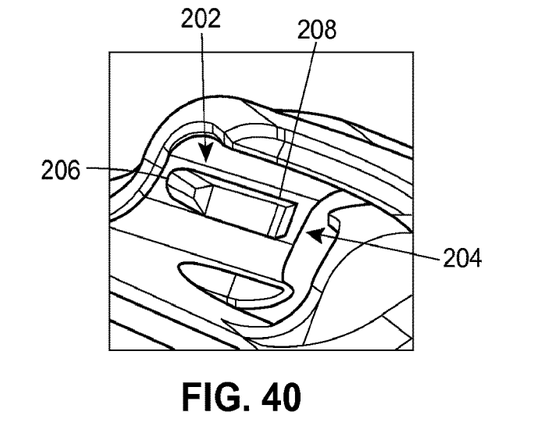
FIG. 40 is an enlarged cross-sectional view illustrating a latch used to attach the insert to the insert port according to an embodiment such as illustrated in FIG. 38.

FIGS. 38-40 illustrate details of the port 200 and insert 210 according to this embodiment of a gas management apparatus. FIGS. 39 and 40 particularly illustrate the latch 202 used to attach the insert to the insert port when the insert is in use. The geometry in the slot is created such that the port curve follows the curve of the smallest diameter of the insert housing. The slot 204 in the port follows the curves of the insert housing, such that odor or output leaks do not occur. The latch 202 includes "on" ramps 206 to assist the user by guiding the part into place, and "off" ramps 208 to facilitate release of the used insert when pressure is applied by the new insert.

The outer, curved lip of the port will be used to provide a means to attach the port to the pouch. A seal can be achieved through adhesive or heat-sealing methods around the entire rim of the port. The curved edges facilitate in creating that seal, as any corners would provide a risk for leakage of odor or output.

It will be recognized that according to the specific nature of a particular embodiment, one or more of the following issues may need to be addressed:

Minimize contact of adsorbent to gas prior to intended use
Allow the user to implement it in a sanitary way
Maximize direct contact of adsorbent with gas in pouch
Minimize contact of adsorbent with liquid/feces in pouch
Function after exposure to fluids between pH 5.8 and 6.8
Be non-toxic to skin or the stoma According to any one or more of the embodiments described herein, one or more of the following advantages may be realized:

Works in the presence of liquid
Decreases gas odor AND volume
Extends time between ostomy pouch evacuation
Improves performance (of volume reduction) at typical operating conditions Further, it will be recognized that one or more of the embodiments described herein may be used in the following alternate environments:

Diapers, diaper pails—for odorous gas adsorption
Bathroom deodorizers—for odorous gas adsorption
Waste management systems—for odorous gas adsorption
Chux—for odorous gas adsorption
Bedside commodes and bedpans—for odorous gas adsorption
Pet training pads & waste management—for odorous gas adsorption
Industrial gas purification systems—for gas separation or storage In conclusion, the detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A gas management apparatus for use with an ostomy pouch, comprising:
an insert port defining an insert-receiving passage in communication with an inner chamber of an ostomy pouch and an exterior of the ostomy pouch, the insert port being integrated into one or more walls of the ostomy pouch;
an insert selectively received in the insert-receiving passage of the insert port, the insert including at least one vent therein; and an odor adsorbent element disposed in the insert, the insert-receiving passage and the vent of the insert defining a pathway for gases passing from the inner chamber of the ostomy pouch and through the odor adsorbent element to pass out of the gas management apparatus;
the insert port including an inner wall and an outer wall, said inner and outer walls defining a groove therebetween, the insert including a hub having a wall received in the groove defined between the inner and outer walls of the insert port; and
a latch provided on at least one of the inner and outer walls of the insert port, the latch securing the insert to the port, the latch being defined by a pair of facing ridges formed on facing surfaces of the inner and outer walls defining the groove of the insert port, and the wall of the hub including a ridge that is lockingly engaged by the facing ridges formed on facing surfaces of the inner and outer walls, thereby securing the hub to the insert port.

2. The gas management apparatus of claim 1, at least a portion of the outer wall being taller than the inner wall, the insert having an outwardly-directed lip region that engages a top of the outer wall and the insert further having an inwardly-directed lip region, the odor adsorbent element secured intermediate the inner wall of the insert port and the inwardly-directed lip region of the insert.

3. The gas management apparatus of claim 1, each of the insert port and the insert having an oblong shape.

4. The gas management system of claim 1, the insert further comprising a pair of outwardly-directed grips to facilitate handling of the insert, an outer wall of the insert port having a pair of grip-receiving channels to receive said grips.

5. A gas management apparatus for use with an ostomy pouch, comprising:
- an insert port defining an insert-receiving passage in communication with an inner chamber of an ostomy pouch and an exterior of the ostomy pouch, the insert port being integrated into one or more walls of the ostomy pouch;
- an insert selectively received in the insert-receiving passage of the insert port, the insert including at least one vent therein; and an odor adsorbent element disposed in the insert, the insert-receiving passage and the vent of the insert defining a pathway for gases passing from the inner chamber of the ostomy pouch and through the odor adsorbent element to pass out of the gas management apparatus;
- the insert port including an inner wall and an outer wall, said inner and outer walls defining a groove therebetween, the insert including a hub having a wall received in the groove defined between the inner and outer walls of the insert port; and
- an o-ring disposed intermediate the insert and the inner and outer walls defining the groove of the insert port.

6. The gas management apparatus of claim 5, at least a portion of the outer wall being taller than the inner wall, the insert having an outwardly-directed lip region that engages a top of the outer wall and the insert further having an inwardly-directed lip region, the odor adsorbent element secured intermediate the inner wall of the insert port and the inwardly-directed lip region of the insert.

7. The gas management apparatus of claim 5, each of the insert port and the insert having an oblong shape.

8. The gas management system of claim 5, the insert further comprising a pair of outwardly-directed grips to facilitate handling of the insert, an outer wall of the insert port having a pair of grip-receiving channels to receive said grips.

9. A gas management apparatus for use with an ostomy pouch, comprising:
- an insert port defining an insert-receiving passage in communication with an inner chamber of an ostomy pouch and an exterior of the ostomy pouch, the insert port being integrated into one or more walls of the ostomy pouch;
- an insert selectively received in the insert-receiving passage of the insert port, the insert including at least one vent therein; and an odor adsorbent element disposed in the insert, the insert-receiving passage and the vent of the insert defining a pathway for gases passing from the inner chamber of the ostomy pouch and through the odor adsorbent element to pass out of the gas management apparatus; and
- a guard having first and second insert-receiving ends, the first insert-receiving end receiving the insert upon removal from the insert-receiving passage of the insert port and the second insert-receiving end carrying a replacement insert to be inserted into the insert-receiving passage of the insert port, the guard including a wall separating the removed insert from the replacement insert and serving to seal the removed insert and the replacement insert.

10. The gas management system of claim 9, the guard including one of an indentation, a recess, or a saddle in an exterior thereof to facilitate handling.

11. The gas management system of claim 9, wherein the guard includes grip-receiving channels in an outer guard wall, the grip-receiving channels being complementary to respective grips of the removed insert and the replacement insert.

12. The gas management apparatus of claim 9, at least a portion of the outer wall being taller than the inner wall, the insert having an outwardly-directed lip region that engages a top of the outer wall and the insert further having an inwardly-directed lip region, the odor adsorbent element secured intermediate the inner wall of the insert port and the inwardly-directed lip region of the insert.

13. The gas management apparatus of claim 9, each of the insert port and the insert having an oblong shape.

14. The gas management system of claim 9, the insert further comprising a pair of outwardly-directed grips to facilitate handling of the insert, an outer wall of the insert port having a pair of grip-receiving channels to receive said grips.

* * * * *

UNITED STATES PATENT AND TRADEMARK OFFICE
CERTIFICATE OF CORRECTION

PATENT NO. : 10,653,551 B2  
APPLICATION NO. : 15/321429  
DATED : May 19, 2020  
INVENTOR(S) : Joan C. Apolinario et al.

It is certified that error appears in the above-identified patent and that said Letters Patent is hereby corrected as shown below:

On the Title Page

Item (73), Line 1, "ENTREMOUS, LLC" should be -- ENTRENOUS, LLC --

Signed and Sealed this
Eighteenth Day of August, 2020

Andrei Iancu
*Director of the United States Patent and Trademark Office*